United States Patent [19]

Milstone et al.

[11] Patent Number: 5,326,764
[45] Date of Patent: Jul. 5, 1994

[54] METHOD FOR THE TREATMENT OF HYPERPROLIFERATIVE DISORDERS

[75] Inventors: Leonard M. Milstone, Hamden; Pauline M. Schwartz, Madison, both of Conn.

[73] Assignee: Yale University, New Haven, Conn.

[21] Appl. No.: 77,152

[22] Filed: Jun. 16, 1993

Related U.S. Application Data

[60] Division of Ser. No. 783,560, Nov. 28, 1991, Pat. No. 5,242,921, which is a continuation of Ser. No. 551,053, Jul. 12, 1990, abandoned, which is a continuation of Ser. No. 187,489, Apr. 27, 1988, abandoned.

[51] Int. Cl.$^5$ .......................................... A61K 31/505
[52] U.S. Cl. ..................................... 514/258; 514/274
[58] Field of Search .................................. 514/274, 258

[56] References Cited

U.S. PATENT DOCUMENTS 5,242,921  9/1993  Milstowe et al. .................. 514/258

Primary Examiner—Jerome D. Goldberg
Attorney, Agent, or Firm—Kenyon & Kenyon

[57] ABSTRACT

The present invention provides new methods for the treatment of hyperproliferative disorders of skin epidermal cells, particularly psoriasis, by administering 5-fluorouracil and dipyridamole, with one or both agents being administered topically at the site of the hyperproliferative disease.

8 Claims, 1 Drawing Sheet

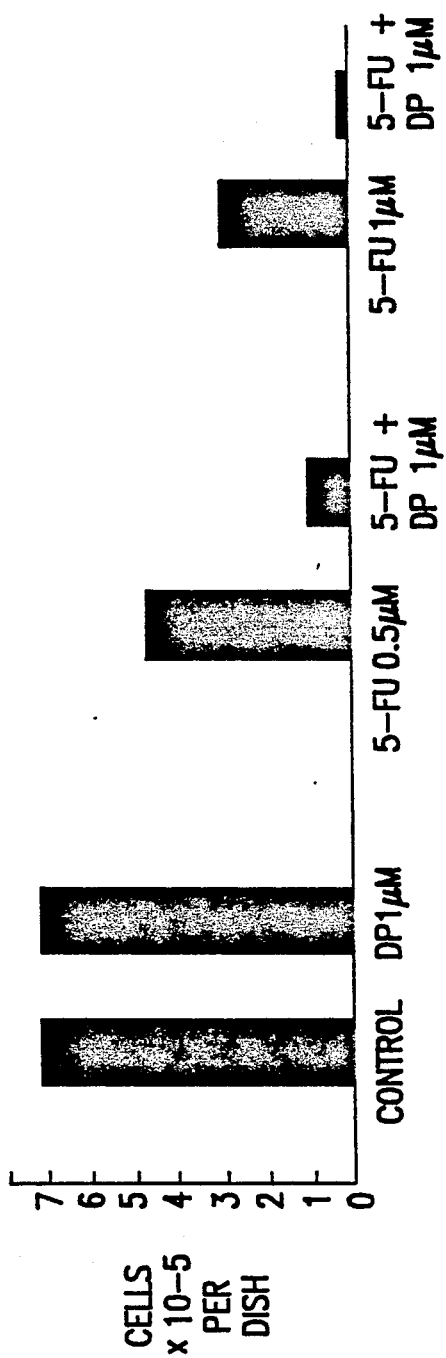
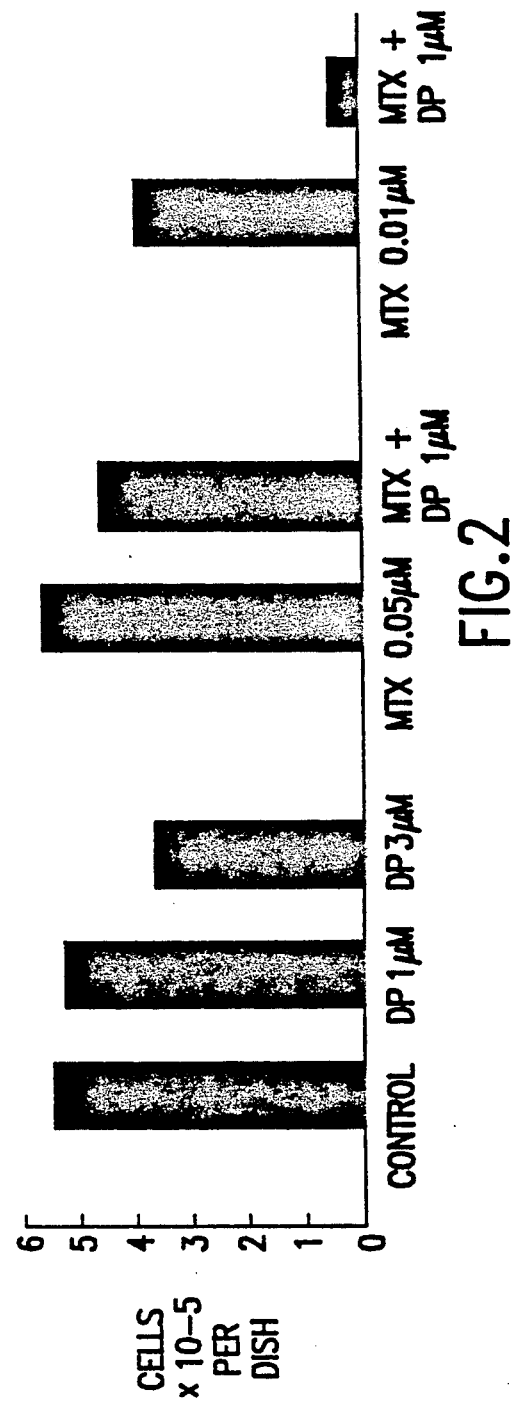

METHOD FOR THE TREATMENT OF HYPERPROLIFERATIVE DISORDERS

This is a division of application Ser. No. 07/783,560 filed 28 Nov. 1991 now U.S. Pat. No. 5,242,921, which is a continuation of application Ser. No. 07/551,053 filed 12 Jun. 1990 now abandoned, which is a file wrapper continuation of application Ser. No. 07/187,489 filed 27 Apr. 1988 now abandoned.

This invention relates to compositions and methods for the treatment of cutaneous diseases such as psoriasis and actinic keratosis in which there is abnormal proliferation or growth of cells of the skin, particularly keratinocytes, and hyperplastic and neoplastic conditions of other epithelial organ systems which are accessible to direct application of a pharmaceutical agent.

BACKGROUND OF THE INVENTION

Normal skin epidermis is a complex epithelial tissue containing keratinocytes that are proliferating, differentiating and desquamating, and is stratified such that morphological and functional changes in the keratinocytes occur in an orderly progression. More specifically, the basal layer of the epidermis contains proliferating keratinocytes which synthesize DNA, while the superbasal layers of the epidermis contain highly differentiated keratinocytes which degrade DNA. Thus, the normal epidermis is maintained in a dynamic steady state as proliferation of keratinocytes continually compensates for the loss of cells which are shed from the surface of the skin.

Many common diseases of the skin epidermis, such as psoriasis, squamous cell carcinoma, keratoacanthoma, actinic keratosis and warts, are characterized by localized abnormal proliferation and growth. For example, in psoriasis, which is characterized by scaly, red, elevated plaques on the skin, the keratinocytes are known to proliferate much more rapidly than normal and to differentiate less completely.

While available treatments for such diseases can be effective, their clinical use is often limited by toxicity, either systemic or local. For example, oral methotrexate, which acts to inhibit de novo DNA synthesis, is probably the most effective treatment presently available for psoriasis, yet it is only rarely used for fear of hepatic or bone marrow toxicity. Hanno et al., J. Am. Acad. Dermatol. 2:171–174 (1980). Local application of purine and pyrimidine analogs or antimetabolites to diseased skin has either failed to work as expected or has produced intolerable local toxicity. For example, topical methotrexate has been deemed ineffective for treatment of psoriasis. Weinstein et al., Arch Dermatol 117: 88–393 (1981). Topical 5-fluorouracil may be an effective treatment for psoriasis, but is usually considered to be unacceptably irritating. Goette, J. Am Acad Dermatol 4:633–649 (1981).

Many of the chemotherapeutic agents which have been used to treat the hyperproliferative diseases of the epidermis have been inhibitors that block de novo synthesis of nucleotide precursors of DNA. These chemotherapeutic agents have sought to block the de novo synthesis of thymidine monophosphate, which, in the cell, is converted in several steps to thymidine triphosphate, one of the four deoxynucleoside phosphates needed by the cell to synthesize DNA.

Another means by which the cell obtains thymidine for DNA synthesis is by the so-called "salvage" mechanism, whereby thymidine is transported into the cell by cell transport mechanisms, e.g., facilitated diffusion. In contrast to the prior attempts to block de novo synthesis, relatively few attempts have been made to control the "salvage" of nucleosides in the cell for any purpose, and there have been no known attempts to control the "salvage" pathway as a means of treating hyperproliferative diseases of the skin.

Thus, prior attempts to treat hyperproliferative diseases of the skin have proven unsuccessful or have been associated with unacceptable toxicity, and there remains a need for safe and efficacious pharmaceutical compositions and methods for the use thereof which eliminate or moderate the hyperproliferative action of cells of the epidermis in diseases such as psoriasis, actinic keratosis and other hyperplastic and neoplastic conditions of the skin and other organ systems, such as the oral cavity and cervix, which are accessible to direct application of a pharmaceutical agent.

SUMMARY OF THE INVENTION

It is thus an object of the present invention to provide pharmaceutical compositions and methods for the use thereof in the treatment of hyperproliferative diseases of the skin and other epithelial tissue.

It is yet another object of the present invention to provide pharmaceutical compositions and methods for the use thereof to inhibit both the de novo and salvage pathways in the synthesis of DNA in skin cells.

It is yet another object of the present invention to provide pharmaceutical compositions and methods for the use thereof which are applied topically to locally treat hyperproliferative diseases of the skin and other epithelial tissue.

It is yet another object of the present invention to provide pharmaceutical compositions and methods for the use thereof in the treatment of hyperproliferative diseases of the skin and other epithelial tissue which limit or eliminate systemic toxic effects.

These and other objects are achieved by the following methods:

A method for the treatment of hyperproliferative disorders of skin epidermal cells which comprises the concurrent administration to a patient of an efficacious amount of an inhibitor of the de novo pathway in DNA synthesis and an efficacious amount of an inhibitor of the salvage pathway in DNA synthesis, wherein the inhibitor of the de novo pathway is 5-fluorouracil and the inhibitor of the salvage pathway is dipyridamole, wherein the dipyridamole is administered topically at the site of the hyperproliferative disease and is applied at a concentration between about 0.1 and about 5 wt. %, and wherein the 5-fluorouracil is administered orally or by injection (preferably, the 5-fluorouracil is orally administered in an amount between about 5 -fluorouracil is orally administered in an amount between about 5 and about 50 mg/week);

A method for the treatment of hyperproliferative disorders of skin epidermal cells which comprises the concurrent administration to a patient of an efficacious amount of an inhibitor of the de novo pathway in DNA synthesis and an efficacious amount of an inhibitor of the salvage pathway in DNA synthesis, wherein the inhibitor of the de novo pathway is 5-fluorouracil and the inhibitor of the salvage pathway is dipyridamole, wherein the 5-fluorouracil is administered topically at the site of the hyperproliferative disease and is applied at a concentration between about 0.1 and about 5 wt. %, m and wherein the dipyridamole is administered orally or by injection;

A method for the treatment of hyperproliferative disorders of skin epidermal cells which comprises the concurrent administration to a patient of an efficacious amount of an inhibitor of the de novo pathway in DNA synthesis and an efficacious amount of an inhibitor of the salvage pathway in DNA synthesis, wherein the inhibitor of the de novo pathway is 5-fluorouracil and the inhibitor of the salvage pathway is dipyridamole, wherein the dipyridamole is administered topically at the site of the hyperproliferative disease and is applied at a concentration between about 0.1 and about 5 wt. %, and wherein the 5-fluorouracil is administered topically at the site of the hyperproliferative disease and is applied at a concentration between about 0.1 and about 5 wt. %.

These methods are particularly useful when the hyperproliferative disorder of epidermal cells is psoriasis.

BRIEF DESCRIPTION OF THE DRAWINGS

FIG. 1 depicts the effect of dipyridamole (DP) and 5-fluorouracil (5-FU) on the growth of human keratinocytes.

FIG. 2 depicts the effect of dypyridamole (DP) and methotrexate (MTX) on the growth of human keratinocytes.

DETAILED DESCRIPTION OF THE INVENTION

The present invention relates to novel methods of us of pharmaceutical compositions for the treatment of psoriasis and other hyperproliferative and neoplastic diseases of the skin and other topically accessible lining epithelia. More specifically, the methods of use of the invention comprise the combined use of inhibitors of de novo and "transport" or "salvage" pathways in DNA synthesis for the treatment of a variety of hyperproliferative disorders of the skin, such as psoriasis, actinic keratosis, squamous cell carcinoma, keratocanthoma, etc.

In accordance with the present invention, it has been surprisingly discovered that the "transport" inhibitors have a synergistic effect on the antiproliferative action of de novo inhibitors when used together to inhibit DNA synthesis in cells of the skin. Both types of these inhibitors of DNA synthesis need to be available to the proliferating cell to exhibit this synergistic effect. Thus, the methods according to the invention should be particularly effective when the affected areas are directly contacted with at least one inhibitor. Accordingly, in a most preferred embodiment, at least one type of these inhibitors is applied topically at the site of the hyperproliferative cell growth so as to increase local efficacy without increasing toxicity in the subject, while the other type of inhibitor may be administered systemically, e.g., orally In a preferred embodiment, both of these types of inhibitors of DNA synthesis are applied topically to the site of the proliferative disease. The invention also contemplates the systemic, e.g., oral, administration of both of these types of inhibitors.

Thus, the method according to the invention is directed to the use of at least one "transport" inhibitor together with at least one "de novo" inhibitor to block DNA synthesis in cells of the skin and other lining epithelia in which abnormally high DNA synthesis, and consequently abnormal cell production, is occurring.

By inhibiting both the de novo and "salvage" pathways, the cell is prevented from compensating for the disruption of de novo DNA synthesis caused by the concurrently administered de novo inhibitor by transporting the nucleoside, e.g., thymidine, into the cell by means of the "salvage" pathway.

In attacking the hyperproliferative cell growth through both the "de novo" and "salvage" mechanisms, the cell is hindered or precluded from producing dTTP, and consequently, DNA. Since no mechanism other than the salvage mechanism is known to exist in the cell whereby the cell can compensate for the loss of de novo nucleoside producing ability, the invention contemplates the simultaneous blocking or hindering of all pathways which permit DNA synthesis in such hyperproliferative cells.

Through the method according to the invention, it is possible to administer one type of inhibitor orally and the other type topically. Because one type of inhibitor potentiates the effect of the other type of inhibitor, it is possible to eliminate or lessen the required dose of the orally administered inhibitor, thereby reducing or eliminating the toxic effects now associated with the use of orally administered pharmaceutical agents. In this regard, the topical administration of both the "transport" and de novo inhibitor at the site of the hyperproliferative disorder would greatly reduce any toxic effects emanating from systemic administration.

De novo inhibitors are those compositions which inhibit DNA synthesis by preventing the synthesis of nucleotides in the cell from amino acids, ATP and $CO_2$. Without limitation, these compositions can generally be classified into three groups: antifolates such as methotrexate and trimetrexate; antimetabolites, such as 5-fluorouracil, 5fluorouridine, 5-fluorodeoxyuridine, phosphon-L-aspartate (PALA) and acivicin; and inhibitors of nucleic acid synthesis which act by other mechanisms, such as adriamycin.

The "transport" inhibitors generally act to block nucleosides, including thymidine, from entering or leaving the cell, thereby preventing the cell from utilizing outside sources of nucleosides to synthesize DNA. These inhibitors of nucleoside transport thus block the "salvage" of extracellular pyrimidine nucleosides and potentiate the inhibitory action of de novo inhibitors of DNA synthesis. By inhibiting the uptake of nucleosides, i.e., thymidine, the nucleoside cannot be converted to dTTP. Without limitation, the nucleoside "transport" inhibitors include compounds such as dipyridamole, dilazep and nitrobenzylthioinosine.

A preferred embodiment of the present invention comprises the use of methotrexate as the de novo inhibitor and dipyridamole as the "transport" inhibitor. This combination has been found to be particularly effective in inhibiting DNA synthesis in skin cells. When it is desired to administer one of the inhibitors systemically, it is preferred that methotrexate be administered orally in an amount less than about 5-50 mg/week, together with the topical administration of dipyridamole in a concentration of about 0.5-5 wt. %. Oral methotrexate treatment for the treatment of psoriasis is already known, and toxicity can be controlled by those skilled in the art. Alternatively, it has been found that 5fluorouracil as the de novo inhibitor may be efficaciously combined with dipyridamole. An exemplary mode of administration would be to administer both inhibitors topically, e.g., 1-5 wt. % 5-fluorouracil and 0.5-5 wt. % dyridamole.

It is contemplated that more than one of each type of inhibitor may be used in the methods according to the invention. Thus, more than one of the "transport" or de novo inhibitors may be utilized in the treatment of a patient, provided toxic levels are taken into consideration by the physician supervising the regimen.

Toxic thresholds vary widely, even between members of each group of inhibitors, and may be easily assessed by those skilled in the art. Since there is minimal concern over toxicity to a subject when one of the inhibitors, either de novo or "transport", is applied topically to an isolated skin site in need of treatment, a wide range of amounts of such inhibitors may be utilized in the invention. For topical application, pharmaceutical compositions of "de novo" and "transport" inhibitors in the range of about 0.1-5 wt. % should generally be effective and non-toxic when coupled with topical or systemic administration of the other inhibitor. For systemic administration, it is contemplated that amounts of an inhibitor equal to or less than the known toxic value for that compound should be utilized when administered together with the topical use of the other inhibitor(s).

The concentration ranges set forth herein are provided by way of description and not by way of limitation since it is recognized that the concentration may be adjusted over a wide range depending on a number of factors. Generally, the efficacious amount and concentration of the inhibitors are those which result in the composition exhibiting the property or properties required in the treatment for which the composition is being used, e.g., psoriasis or actinic keratosis The preferred amounts depend upon the particular condition being treated, the severity of the condition, the method of delivery to the treatment site, e.g., topical or systemic, the rate of delivery of the active ingredients to the treatment site, the number of applications of the formulation which can be used, the other inhibitor used, the carrier material, etc Preferred amounts for any specific application may be determined by normal pharmacological screening methods used in the art.

It has also been found that it is necessary to treat the hyperproliferative cells with at least a threshold amount of each type of inhibitor to observe an inhibition of the hyperproliferative cell activity, and the minimum effective amount will depend on the inhibitor used.

Generally, preferred amounts of inhibitors with respect to two types of hyperproliferative disease are shown in Table I.

TABLE I

| Treatment/ Use | Preferred Amount of Topical Inhibitor | Preferred Amount of Systemic Inhibitor | Exemplary Application Amount/Rate of Inhibitor |
|---|---|---|---|
| Psoriasis | .1 to 5 wt. % inhibitor (e.g., dypyamole) | 5 to 50 mg/wk inhibitor (e.g., methotrexate) | Apply at least one inhibitor topically at the desired site, while at approximately the same time administer the other inhibitor orally, |
| actinic keratosis | 0.1 to 5 wt. % inhibitor (e.g., 5-fluorouracil) | 5 to 50 mg. t.i.d. inhibitor (e.g., dipyridamole) | three times a day. Repeat application of topically administered inhibitor as needed, avoiding |

TABLE I-continued

| Treatment/ Use | Preferred Amount of Topical Inhibitor | Preferred Amount of Systemic Inhibitor | Exemplary Application Amount/Rate of Inhibitor |
|---|---|---|---|
| | | | toxic blood levels. Healing period may extend for several weeks. When two inhibitors are applied topically, apply in amounts needed depending on rate of absorption by skin. |

The topically administered inhibitor(s) is usually formulated with a pharmaceutically-acceptable carrier. Carrier materials are well known in the pharmaceutical formulation art and include those materials referred to as diluents or vehicles. The carriers may include inorganic or organic materials and should have sufficient viscosity to allow spreading of the composition and provide good adherence to the skin. Examples of such carriers include polyols such as glycerol, propylene glycol, polyethylene glycol, and other materials well known to those skilled in this art.

In addition to the inhibitor(s) and carrier, the topical formulation can contain pharmacologically-acceptable additives or adjuvants such as antimicrobial agents, e.g., methyl, ethyl, propyl, and butyl esters of parahydroxybenzoic acid as well as benzyl alcohol, chlorobutanol, phenol, ascorbic acid, etc. The formulation can also contain thickening agents, coloring agents, buffers, stabilizers and preservatives including antioxidants such as butyl hydroxyanisole in accordance with the practice of the art. The formulation can also contain penetration enhancers such as dimethyl sulfoxide, long-chain alcohols such as monoxynol, long-chain carboxylic acids, propylene glycol, N-(2-hydroxyethyl)pyrrolidone, 1-dodecyl-azacycloheptan-2-one, and the like. Depending on the method of application and the disease being treated, it may be desirable to use absorption-delaying agents such as aluminum monostearate and gelatin.

The topical compositions of the invention can be adjusted using components well-known in the formulation art to provide a pharmaceutical formulation which is a gel, cream, ointment, solid, liquid, semi-solid, etc. The particular physical form of the formulation depends on the desired method of treatment and the patient to be treated. Typical pharmaceutical formulations according to the invention are set

TABLE II

| Application Form | Formulation | Grams |
|---|---|---|
| Ointment | Methotrexate | 2.5 |
| | Dipyridamole | 2.5 |
| | PEG 400 | 4.2 |
| | PEG 8000 | 61.7 |
| | Water | 29.0 |
| | Asorbic Acid | 0.1 |
| Cream | Methotrexate | 5.0 |
| | Asorbic acid | 0.1 |
| | Benzyl alcohol | 5.0 |
| | Propylene glycol | 23.0 |
| | Water | 35.4 |
| | Stearyl alcohol | 7.0 |
| | Cetyl alcohol | 4.5 |
| | White petrolatum | 13.0 |
| | Poloxyl-40 stearate | 7.0 |
| Gel | Dipyridamole | 5.0 |
| | Standard denatured alcohol | 12.0 |

TABLE II-continued

| Application Form | Formulation | Grams |
| --- | --- | --- |
| | Propylene glycol | 22.5 |
| | Water | 50.4 |
| | Non-ionic surfactant | 6.0 |
| | Xantham gum | 4.0 |
| | Ascorbic acid | 0.1 |

The concentration of active ingredients in a particular formulation required to provide a particular effective does may be determined by a person skilled in the pharmaceutical formulation art based upon the properties of the carrier and the particular additives introduced into the formulation. It is contemplated that formulations can be prepared that have significantly higher concentrations of one or more of the inhibitors depending upon the carrier and additives being used, as well as the amount of inhibitor being given orally, if any.

If the carrier substantially retains the inhibitor or releases it at a slow rate into the skin, the concentrations of the inhibitor in the formulation can be substantially increased in order to provide an effective treatment. In practice, it is preferred that a formulation contain the lowest concentrations of inhibitor which effectively acts together with the other inhibitor to treat the condition with the desired number of applications, i.e., a lower effective dose rate can be tolerated if multiple applications are used. This low concentration limit is dependent upon the delivery effectiveness of the carrier vehicle.

In preparing a formulation suitable for topical application, the inhibitor is normally mixed with a suitable solvent. Examples of solvents which are effective for this purpose include ethanol, acetone, acetic acid, acidic solutions, dimethyl sulfoxide, glycerine, glycerol, propylene glycol, monoxynol, ethyl ether, polyethylene glycol, etc.

The following examples are included by way of illustration and not by way of limitation.

EXAMPLE 1

Preparation of Cell Culture

Primary cultures of human neonatal foreskin keratinocytes were grown on a feeder layer of irradiated 3T3 cells. Foreskins were dissected to remove subcutaneous tissue. The epidermis and remaining dermis were floated with the epidermis up in 0.25% trypsin at 4° C. for 18-24 hours. The epithelial sheet was peeled from the dermis and the cells were released by gentle vortexing. One foreskin yielded approximately $2-8\times10^6$ cells. Cells were seeded in 100 mm plastic dishes which contained a feeder-layer of $2\times10^6$ lethally irradiated 3T3 cells. Cells were seeded in Dulbecco's Modified Eagle's Medium ("DMEM") in the absence of epidermal growth factor and cholera toxin. Cells were fed with fresh medium twice each week with complete DMEM containing epidermal growth factor and cholera toxin after the second feeding. The cells were passaged after 10-14 days just before the keratinocyte sheet became confluent. The remaining 3T3 cells were removed by vigorous washing with 0.2% EDTA and a single cell suspension was prepared with 0.5% trypsin-0.2% EDTA.

Complete medium consisted of Dulbecco's Modified Eagle's Medium supplemented with 20% Fetal bovine serum, hydrocortisone (0.4 ug/ml), epidermal growth factor (10 ng/ml), cholera toxin (100pM), penicillin (100 u/ml) and streptomycin (100 ug/ml). The Ca++ concentration was 1.8mM.

3T3 cells (ATCC CCL #92) were grown in DMEM with 10% calf serum. Confluent cultures were x-irradiated (1000 rads) and subcultured with trypsin To prepare secondary, stratified cultures, approximately $2-4\times10^5$ cells were plated onto a feeder layer of lethally irradiated 3T3 cells in 35 mm plastic dishes. Secondary cultures become confluent within 2-3 weeks, forming a stratified sheet of 5-7 cell layers. Cultures in which there was microscopic evidence of fibroblasts were discarded.

To prepare secondary exponentially growing monolayer cultures, $2\times10^4$ keratinocytes from primary cultures were seeded into 35 mm dishes with complete MCDB-153. Complete MCDB-153 was basal MCDB 153 medium supplemented with epidermal growth factor (5ng/ml), insulin (5ug/ml), hydrocortisone (0.4ug/ml), ethanolamine (0.1mM), phosphoethanolamine (0.1mM), transferrin (10ug/ml), bovine pituitary extract (50ug protein/ml) and additional amino acids (glutamine ($1.2\times10^{-2}$M), histidine ($2.4\times10^{-4}$M), isoleucine ($7.5\times10$-4M), methionine ($9\times10^{-5}$M), phenylalanine ($9\times10^{-5}$M), trytophan ($4.5\times10^{-5}$M) and tyrosine ($7.5\times10^{-5}$M). The Ca++ concentration was 0.03mM. These cultures were re-fed the day after seeding with control and experimental media.

Basal MCDB-153 contained 3uM thymidine. MCDB-153 without thymidine was formulated by Clonetics, Inc. (Boulder, CO).

EXAMPLE 2

Assay of Thymidine Transport

A suspension of keratinocytes produced by the method described in Example I was shaken in a water bath at 37° C. in medium with or without inhibitors. Ten minutes after the addition of $^3$H-thymidine (4uCi/ml, at various concentrations), a 200 microliter sample of cell suspension was layered on top of a 400 microliter microfuge tube prepared with layer of oil (Parafin Silicon, 16:84) on top of a layer of 3N perchloric acid; preliminary studies showed that within 10 minutes thymidine transport had reached equilibrium. The tube was centrifuged (13,000 rpm for 1 min.) and then frozen at −70° C. The frozen tube was cut through the oil partition and the upper and lower portions placed in separate scintillation vials and counted. Radioactivity in the perchloric acid fraction was associated with intracellular material.

These procedures revealed that $^3$H-thymidine enters keratinocytes from the medium.

EXAMPLE 3

Effect of Dypyridamole on Thymidine Incorporation into DNA.

0.5 micromolar dypyridamole was applied to the culture described in Example 1 containing 3H-thymidine (0.2 micromolar, 4uCi/ml) It was determined by scintillation counting of the trichloroacetic acid-insoluble perchloroacetic acid-hydrolyzable material that the incorporation of $^3$H-thymidine into the DNA of keratinocytes over a two hour period was reduced by 48% due to the presence of dipyridamole.

EXAMPLE 4

Effect of Dipyridamole on Thymidine Transport

One micromolar dipyridamole (Sigma, St. Louis, Mo.) was applied to the culture described in Example 1 containing $^3$H-thymidine (0.2 micromolar, 4uCi/ml) (Moravek Biochemicals, Brea, CA). It was determined by scintillation counting of cells exposed to $^3$H-thymidine in the presence or absence of dipyridamole that dipyridamole inhibited the transport of $^3$H-thymidine into keratinocytes by over 50% over a ten minute period.

EXAMPLE 5

Effect of Methotrexate and 5-Fluorouracil on de novo Pyrimidine Biosynthesis

A cell culture was prepared as in Example 1. 0.1 micromolar methotrexate, available from Sigma, St. Louis, Mo., was applied to the culture. To a separate culture, 0.5 micromolar 5-fluorouracil (Sigma, St. Louis, Missouri) was applied. It was determined by counting the cells after seven days that methotrexate inhibited the growth of keratinocytes by 32% and 5-fluorouracil inhibited cell growth by 30%.

EXAMPLE 6

Effect of combination of dipyridamole with methotrexate and with 5-fluorouracil on cell growth Cell cultures were prepared as in Example 1. A composition of 0.5 micromolar 5-fluorouracil and 1 micromolar dipyridamole was applied to the cell culture. As determined by counting the cells, cell growth was inhibited by 86% over a seven day period These results are illustrated in FIG. 1.

Similarly, a composition of 0.1 micromolar methotrexate and 1 micromolar dipyridamole, when applied to a separate cell culture prepared in accordance with Example 1, demonstrated a 93% inhibition of growth of keratinocytes over a seven day period, as determined by counting the cells. These results are illustrated in FIG. 2.

While there have been described what are presently believed to be preferred embodiments of the invention, it will be apparent to a person skilled in the art that numerous changes can be made in the ingredients, conditions and proportions set forth in the foregoing embodiments without departing from the invention as described herein and as defined in the appended claims.

What is claimed is:

1. A method for the treatment of hyperproliferative disorders of skin epidermal cells which comprises the concurrent administration to a patient of an efficacious amount of an inhibitor of the de novo pathway in DNA synthesis and an efficacious amount of an inhibitor of the salvage pathway in DNA synthesis, wherein the inhibitor of the de novo pathway is 5-fluorouracil and the inhibitor of the salvage pathway is dipyridamole, wherein the dipyridamole is administered topically at the site of the hyperproliferative disease and is applied at a concentration between about 0.1 and about 5 wt. %, and wherein the 5-fluorouracil is administered orally or by injection.

2. The method according to claim 1 wherein the 5-fluorouracil is orally administered in an amount between about 5 and about 50 mg/week.

3. A method for the treatment of hyperproliferative disorders of skin epidermal cells which comprises the concurrent administration to a patient of an efficacious amount of an inhibitor of the de novo pathway in DNA synthesis and an efficacious amount of an inhibitor of the salvage pathway in DNA synthesis, wherein the inhibitor of the de novo pathway is 5-fluorouracil and the inhibitor of the salvage pathway is dipyridamole, wherein the 5-fluorouracil is administered topically at the site of the hyperproliferative disease and is applied at a concentration between about 0.1 and about 5 wt. %, and wherein the dipyridamole is administered orally or by injection.

4. A method for the treatment of hyperproliferative disorders of skin epidermal cells which comprises the concurrent administration to a patient of an efficacious amount of an inhibitor of the de novo pathway in DNA synthesis and an efficacious amount of an inhibitor of the salvage pathway in DNA synthesis, wherein the inhibitor of the de novo pathway is 5-fluorouracil and the inhibitor of the salvage pathway is dipyridamole, wherein the dipyridamole is administered topically at the site of the hyperproliferative disease and is applied at a concentration between about 0.1 and about 5 wt. %, and wherein the 5-fluorouracil is administered topically at the site of the hyperproliferative disease and is applied at a concentration between about 0.1 and about 5 wt. %.

5. The method according to claim 1 wherein the hyperproliferative disorder of epidermal cells is psoriasis.

6. The method according to claim 2 wherein the hyperproliferative disorder of epidermal cells is psoriasis.

7. The method according to claim 3 wherein the hyperproliferative disorder of epidermal cells is psoriasis.

8. The method according to claim 4 wherein the hyperproliferative disorder of epidermal cells is psoriasis.

* * * * *

UNITED STATES PATENT AND TRADEMARK OFFICE
CERTIFICATE OF CORRECTION

PATENT NO. : 5,326,764
DATED : July 5, 1994
INVENTOR(S) : Leonard M. Milstone, et. al.

It is certified that error appears in the above-indentified patent and that said Letters Patent is hereby corrected as shown below:

| Column | Line | |
|---|---|---|
| 1 | 18 | Insert --This invention was made with government support under grant number AR 37549 awarded by the Department of Health and Human Services. The government has certain rights in the invention.-- |
| 2 | 55 | After "5" delete "-fluoroura-". |
| 2 | 56 | Delete entire line. |
| 3 | 1 | Before "and" delete "m". |
| 3 | 22 | Change "us" to --use--. |
| 4 | 35 | Change "5fluorouridine" to --5-fluorouridine--. |

UNITED STATES PATENT AND TRADEMARK OFFICE
CERTIFICATE OF CORRECTION

PATENT NO. : 5,326,764
DATED : July 5, 1994
INVENTOR(S) : Leonard M. Milstone, et. al.

It is certified that error appears in the above-indentified patent and that said Letters Patent is hereby corrected as shown below:

| Column | Line | |
|---|---|---|
| 4 | 64 | Change "5fluorouracil" to --5-fluorouracil--. |
| 4 | 68 | Change "dyridamole" to --dipyridamole--. |
| 5 | 39 | After "etc" insert --.--. |
| 5 | 59 | After "(e.g.," change "dypy-" to -- dipyrid- --. |
| 6 | 51 | After "set" insert --forth in Table II.--. |
| 6 | 59 | Change "Asorbic" to --Ascorbic--. |
| 6 | 61 | Change "Asorbic" to --Ascorbic--. |
| 7 | 6 | Change "Xantham" to --Xanthan--. |

UNITED STATES PATENT AND TRADEMARK OFFICE
CERTIFICATE OF CORRECTION

PATENT NO. : 5,326,764
DATED : July 5, 1994
INVENTOR(S) : Leonard M. Milstone, et. al.

It is certified that error appears in the above-indentified patent and that said Letters Patent is hereby corrected as shown below:

| Column | Line | |
|---|---|---|
| 8 | 1 | Change "Ca++" to --$Ca^{++}$--. |
| 8 | 23 | Change "(7.5x10-4M)" to --$(7.5x10^{-4}M)$--. |
| 8 | 24 | Change "trytophan" to --tryptophan--; change "tyrc-" to -- tyro- --. |
| 8 | 25 | Change "$(7.5x10^{-5}M)$" to --$(7.5x10^{-5}M)$--; change "Ca++" to --$Ca^{++}$--. |
| 8 | 41 | After "(Parafin" insert --:--. |

Signed and Sealed this

First Day of November, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,326,764
DATED : July 5, 1994
INVENTOR(S) : Leonard M. Milstone, et. al.

It is certified that error appears in the above-indentified patent and that said Letters Patent is hereby corrected as shown below:

| Column | Line | |
|---|---|---|
| 1 | 18 | Insert --This invention was made with government support under grant number AR 37549 awarded by the Department of Health and Human Services. The government has certain rights in the invention.-- |
| 2 | 55 | After "5" delete "-fluoroura-". |
| 2 | 56 | Delete entire line. |
| 3 | 1 | Before "and" delete "m". |
| 3 | 32 | Change "us" to --use--. |
| 4 | 35 | Change "5fluorouridine" to --5-fluorouridine--. |

UNITED STATES PATENT AND TRADEMARK OFFICE
CERTIFICATE OF CORRECTION

PATENT NO. : 5,326,764
DATED : July 5, 1994
INVENTOR(S) : Leonard M. Milstone, et. al.

It is certified that error appears in the above-indentified patent and that said Letters Patent is hereby corrected as shown below:

| Column | Line | |
|---|---|---|
| 4 | 64 | Change "5fluorouracil" to --5-fluorouracil--. |
| 4 | 68 | Change "dyridamole" to --dipyridamole--. |
| 5 | 39 | After "etc" insert--.--. |
| 5 | 59 | After "(e.g.," change "dypy-" to -- dipyrid- --. |
| 6 | 51 | After "set" insert --forth in Table II.--. |
| 6 | 59 | Change "Asorbic" to --Ascorbic--. |
| 6 | 61 | Change "Asorbic" to --Ascorbic--. |
| 7 | 6 | Change "Xantham" to --Xanthan--. |

UNITED STATES PATENT AND TRADEMARK OFFICE
CERTIFICATE OF CORRECTION

PATENT NO. : 5,326,764
DATED : July 5, 1994
INVENTOR(S) : Leonard M. Milstone, et. al.

It is certified that error appears in the above-indentified patent and that said Letters Patent is hereby corrected as shown below:

| Column | Line | |
|---|---|---|
| 8 | 1 | Change "Ca++" to --$Ca^{++}$--. |
| 8 | 23 | Change "(7.5x10-4M)" to --(7.5x$10^{-4}$M)--. |
| 8 | 24 | Change "trytophan" to --tryptophan--; change "tyrc-" to -- tyro- --. |
| 8 | 25 | Change "(7.5x$10^{-5}$M)" to --(7.5x$10^{-5}$M)--; change "Ca++" to --$Ca^{++}$--. |
| 8 | 41 | After "(Parafin" insert --:--. |

This certificate supercedes Certificate of Correction issued November 1, 1994.

Signed and Sealed this

Twenty-eight Day of February, 1995

Attest:

BRUCE LEHMAN

Attesting Officer   Commissioner of Patents and Trademarks